(12) United States Patent
Deflorian et al.

(10) Patent No.: US 12,370,281 B2
(45) Date of Patent: Jul. 29, 2025

(54) DEVICE FOR EVAPORATING VOLATILE SUBSTANCES

(71) Applicant: ZOBELE HOLDING SPA, Trento (IT)

(72) Inventors: Stefano Deflorian, Trento (IT); Walter Sordo, Trento (IT)

(73) Assignee: ZOBELE HOLDING SPA, Trento (IT)

( * ) Notice: Subject to any disclaimer, the term of this patent is extended or adjusted under 35 U.S.C. 154(b) by 666 days.

(21) Appl. No.: 17/626,421

(22) PCT Filed: Jul. 12, 2019

(86) PCT No.: PCT/EP2019/068851
§ 371 (c)(1),
(2) Date: Jan. 11, 2022

(87) PCT Pub. No.: WO2021/008670
PCT Pub. Date: Jan. 21, 2021

(65) Prior Publication Data
US 2022/0249726 A1 Aug. 11, 2022

(51) Int. Cl.
*A61L 9/03* (2006.01)
(52) U.S. Cl.
CPC .......... *A61L 9/037* (2013.01); *A61L 2209/13* (2013.01)
(58) Field of Classification Search
CPC ........ A01M 1/00; A01M 1/20; A01M 1/2022; A01M 1/2027; A01M 1/2044; A01M 1/2055; A01M 1/2061; A01M 1/2077; A61L 9/00; A61L 9/015; A61L 9/02; A61L 9/03; A61L 9/037; A61L 9/04; A61L 9/042; A61L 9/12; A61L 9/127; A61L 2209/00; A61L 2209/10; A61L 2209/13
See application file for complete search history.

(56) References Cited

U.S. PATENT DOCUMENTS 7,597,309 B1 * 10/2009 Stucki .................... A61L 9/125
361/37

FOREIGN PATENT DOCUMENTS

| EP | 2460424 A1 | 6/2012 | |
| WO | WO-2006061803 A1 * | 6/2006 | .......... A01M 1/2044 |
| WO | 2021008670 A1 | 1/2021 | |

OTHER PUBLICATIONS

International Search Report and Written Opinion for PCT/EP2019/068851 mailed Jan. 1, 2021.

* cited by examiner

*Primary Examiner* — Natasha E Young
(74) *Attorney, Agent, or Firm* — Kutak Rock LLP

(57) ABSTRACT

The device for evaporating volatile substances comprises a container (1) housing a liquid with the volatile substances, and wick (2) in contact with said liquid and extending outside said container (1), wherein the device also comprises a porous element (3) placed inside the container (1) that is impregnated with said liquid with the volatile substances. The presence of the porous element inside the container permits to place the evaporation device according to the present invention in any suitable position, preventing the leakage of the liquid and still allowing its correct performance.

16 Claims, 6 Drawing Sheets

DEVICE FOR EVAPORATING VOLATILE SUBSTANCES

This is the United States National Stage of Patent Cooperation Treaty Application No. PCT/EP2019/068851, now WO 2021/008670, filed Jul. 12, 2019 the disclosure of which is incorporated herein by reference in its entirety.

The present invention refers to a device for evaporating volatile substances, comprising a wick through which the volatile substances are evaporated.

BACKGROUND OF THE INVENTION

Although numerous alternative constructions have appeared in the last decades in the market of volatile substance dispensers, wick-based diffusers are still the ones having the biggest share on the market.

The wick-based devices exist in several configurations, such as stand alone to be put on a table for example, car versions to be mounted on the grid and plug-ins devices, etc.

For these last two configurations, the devices use to have rotatable features in order to allow the bottle to be placed in the correct vertical position independently of the orientation of the car grid or of the plug mains.

Nevertheless, with the improvement of capacity of battery (rechargeable or not) and also the appearance of more and more new kinds of devices (like for example connected devices), there is a necessity to have a system that can works in whatever position.

A big problem with devices provided with wicks is that the liquid comprising the volatile substances can leak when a certain degree of inclination is reached from a correct vertical position.

Leaking of this liquid can be a problem for the furniture where the device is used but also could attack the internal part of the device, that can be electrical and could provoke an electrical malfunction that could even lead to a fire.

Therefore, one purpose of the present invention is to provide a device for evaporating volatile substances that permits to be placed in any position.

DESCRIPTION OF THE INVENTION

With the device according to the present invention it is possible to solve said drawbacks, providing other advantages that are described below.

The device for evaporating volatile substances according to the present invention comprises:
 a container housing a liquid with the volatile substances, and
 a wick in contact with said liquid and extending outside said container,
 wherein the device also comprises a porous element placed inside the container that is impregnated with said liquid with the volatile substances.

The presence of the porous element inside the container permits to place the evaporation device according to the present invention in any suitable position, preventing the leakage of the liquid and still allowing its correct performance.

Advantageously, all the liquid is impregnated in the porous element.

According to a preferred embodiment, the porous element is a sponge, e.g. made from a polymeric substrate.

Furthermore, the container of the evaporation device according to the present invention comprises a cover, wherein said cover or container comprises a hole through which said wick is passed.

To seal the device, the cover or container preferably comprises a stopper placed around the hole in contact with the wick.

Furthermore, according to a preferred embodiment, the porous element is compressed inside the container and the wick extends substantially along the whole container.

Advantageously, the device also comprises venting means for venting the container. Preferably, the venting means comprises at least a vent placed on the container and/or on the stopper.

According to a preferred embodiment, the venting means comprises a plurality of vents placed on the top and bottom portions of the container and/or on the side portion of the container.

The device according to the present invention can also comprise an additional body placed symmetrically with respect to the wick.

Furthermore, the device can also comprise a heater, which is preferably placed close or next to the wick, e.g. placed equidistantly from the container and the additional body.

The venting means avoids the temperature rising due to environmental temperature or due to the effect of the heater, preventing the formation of steam inside the container, especially if a little space has been left between the porous element and the bottom of the container, preventing leakages.

BRIEF DESCRIPTION OF THE DRAWINGS

For a better understanding the above explanation and for the sole purpose of providing an example, some non-limiting drawings are included that schematically depict a practical embodiment.

DESCRIPTION OF PREFERRED EMBODIMENTS

Figure 1:
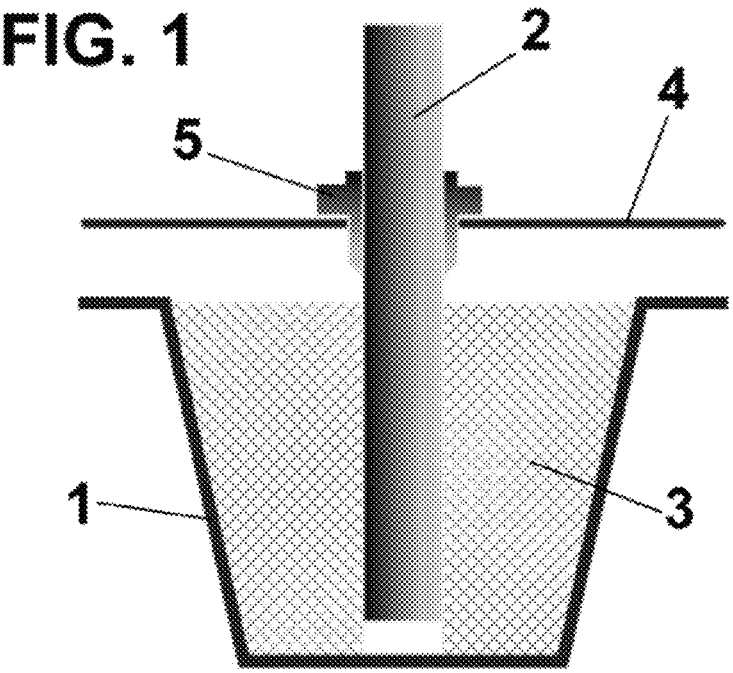
FIG. 1 is an elevation cross-section view of the device of the present invention, according to a first embodiment.

The device for evaporating volatile substances according to the present invention comprises a container 1 that houses liquid with said volatile substances and a wick 2 in contact with the liquid.

Said wick 2 preferably extends from the bottom of the container 1 in contact with the liquid and outside of the container 1, where evaporation occurs (which can be promoted by additional means like heaters (shown in FIG. 7) or fans (not shown in the drawings)).

According to the present invention, the liquid is not free flowing inside the container 1, but it is contained or impregnated in a porous element 3 (e.g. a sponge).

This way the feeding of the wick is only due to capillarity through the porous element 3 and the capillar connection between the porous element 3 and the wick 2, and not anymore linked to gravity, as occurs with container with free-flowing liquids.

Thanks to that, the transportation to the evaporation area of the wick 2 is similar independently of the position of the device.

The wick 2 can be whatever wick currently used in this kind of product, but preferably is a high capillarity wick made of fibers or sintered plastics.

The porous element can be made from a felt, a cellulosic part or an open cell polymeric material. Felt can be made from wool, synthetic fibers or thermally bonded fibers. The open cell polymeric material can be made of polyurethane, silicone, EPDM, melamine or other materials known for this kind of applications having chemical resistance to fragrances or solvents.

Preferably, the porous element density is lower than 0.05 g/cm3.

Also, preferably the volumetric ratio between liquid absorbed and foam material is higher than 10.

The container 1 also comprises preferably a cover 4 in such a way the porous element 3 can be introduced in the container 1 substantially not deforming it. Even though in FIGS. 1-3 the cover 4 is shown not in contact with the container 1, it is use position it is in contact with the container 1, as shown in FIG. 4.

Preferably, the cover 4 has a hole to allow the wick to pass through it, and a stopper 5 to guarantee the sealing between the wick and the cover, as shown in the first embodiment of FIG. 1.

Figure 2:
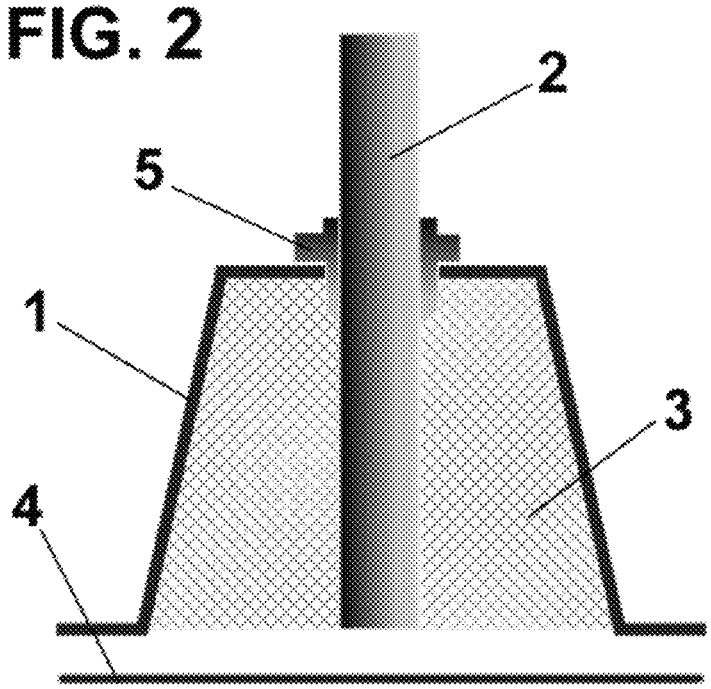
FIG. 2 is an elevation cross-section view of the device of the present invention, according to a second embodiment.

In a second embodiment, the upper part of the container 1 is of reduced dimensions and the lower part of the container 1 is progressively widening in order to have a biased profile (FIG. 2).

This biased profile is to reduce obstruction of the vapors when the container 1 is placed above the evaporation surface. This is particularly relevant when the container is used together with a heater as hot vapors tends to condensate on the surfaces found on their way out of the device if the flow is not easy.

Therefore, in this embodiment, the profile of the container is mainly conical or pyramidal and the cover 4 is in fact the base of the cone or pyramid.

The porous element 3 in these embodiments can be made, for example, of an absorbent cellulosic substrate, a fibrous polymeric structure or an open cell polymeric foam.

The porous element 3 preferably fills all the inner space of the container 1 (apart the space taken by the wick 2). Alternatively, the porous element 3 can also leave part of the inner space of the container 1 free.

Figure 3:
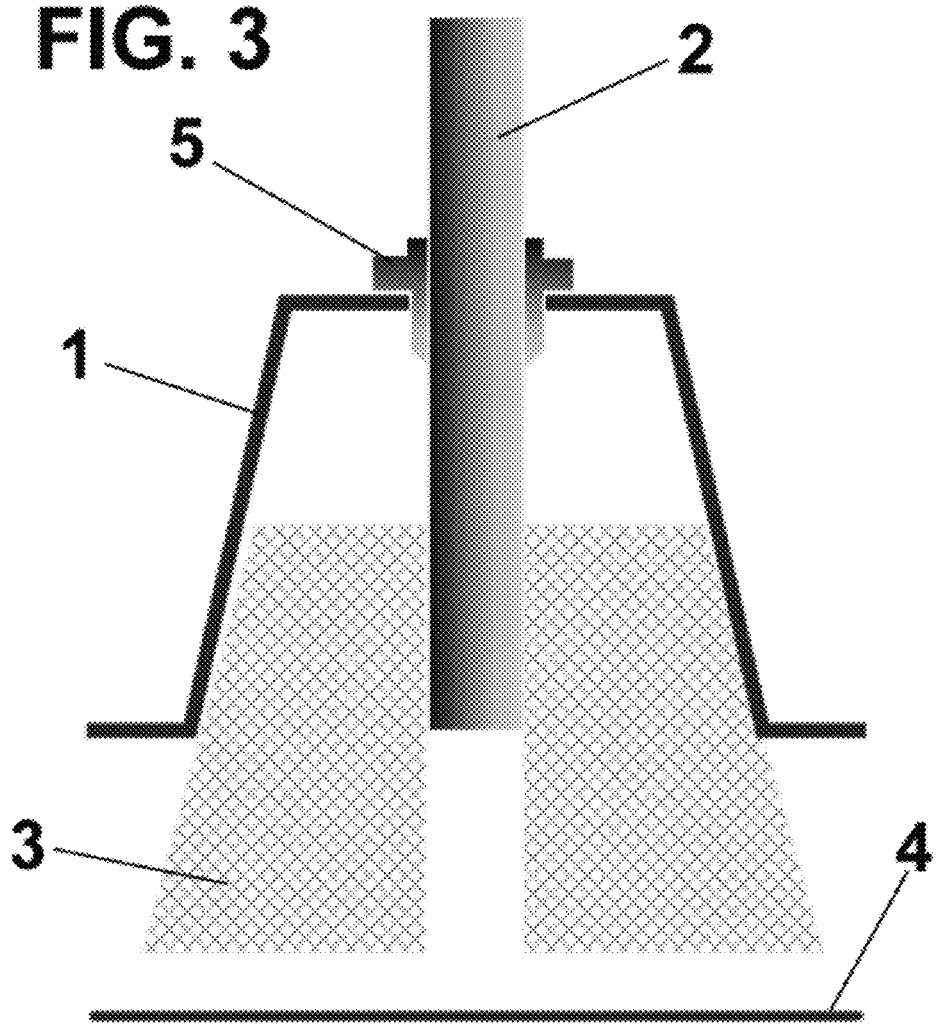
FIG. 3 is an elevation cross-section view of the device of the present invention, according to a third embodiment, before the insertion of the porous element inside the container.
Figure 4:
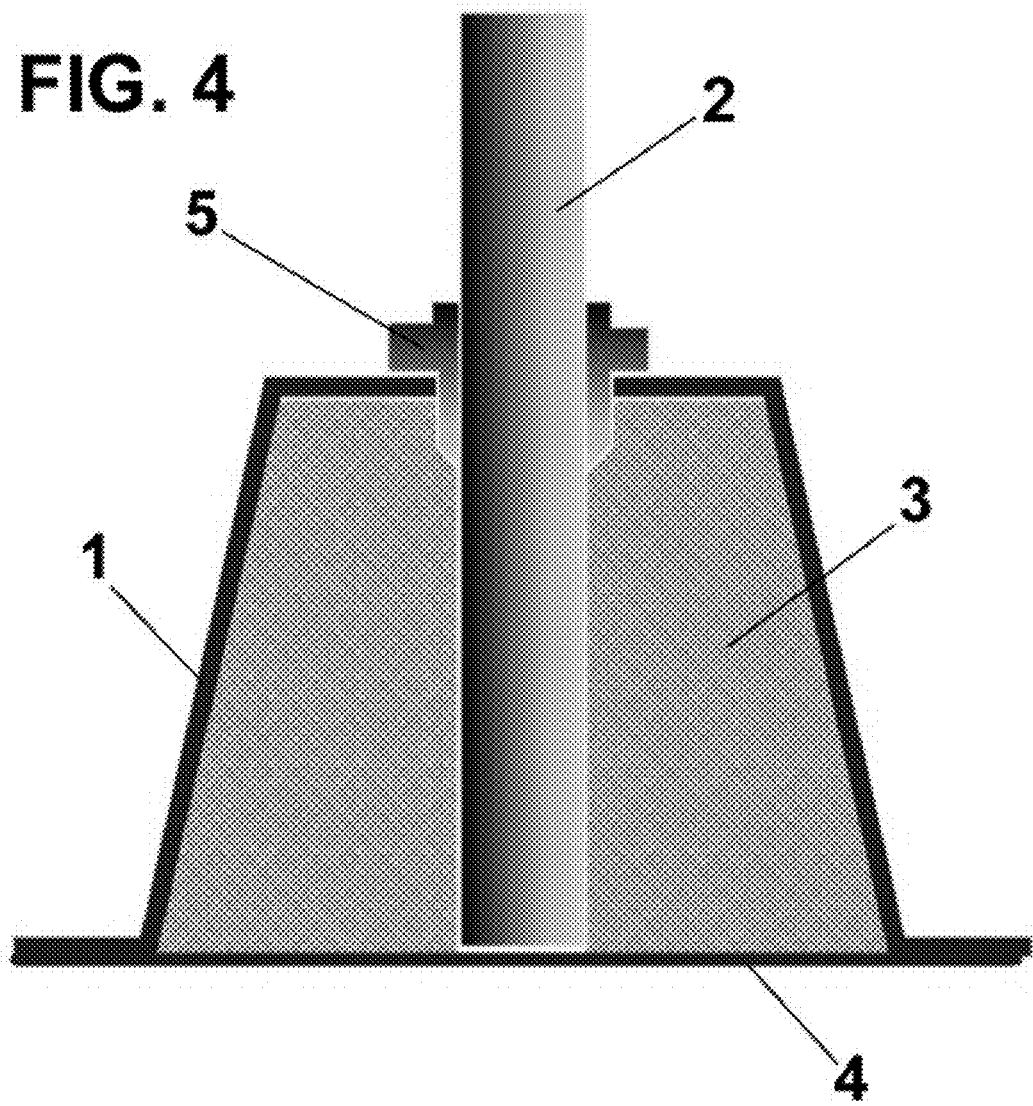
FIG. 4 is an elevation cross-section view of the device of the present invention, according to a third embodiment, after the insertion of the porous element inside the container, in its use position.

In a third embodiment shown in FIGS. 3 and 4, the design of the porous element 3 is not, or only partially, similar to the inner space of the container, and it is compressed before and/or during its introduction in the container 1.

It is clear that the contact between the porous element 3 and the wick 2 is critical to assure a good capillary connection of the volatile substance between them.

By compressing the porous element 3, the contact will be forced between the wick 2 and said porous element 3 in order to assure the correct contact.

Of course, the compression of the porous element 3 modifies its pore size and also its absorption capacity.

It is important then that the amount of liquid dosed inside the porous element 3 does not exceeds the absorption capacity of the porous element 3 in its compressed state, in order to avoid the liquid to be ejected from the porous element 3 when the porous element 3 is introduced and compressed in the container 1.

Regarding the connection between the porous element 3 and the wick 2, according to one embodiment, the porous element 3 is designed to have a hole with similar dimensions and shape that the wick 2 so that the wick 2 can fit in the porous element 3.

Alternatively, the hole in the porous element 3 is quite bigger than the wick 2 and the porous element 3 is pressed against the wick 2 when it is compressed during its introduction in the container 1.

Still alternatively, the hole is the porous element 3 is a simple flat cut, preferably passing through the whole porous element length. The porous element 3 is compressed against the wick 2 when the wick 2 is introduced in the porous element 3.

Figure 5:
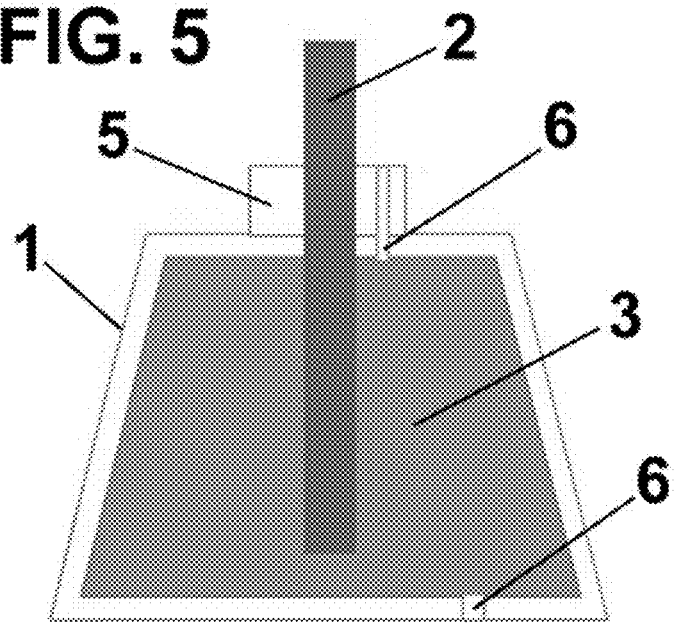
FIG. 5 is a diagrammatical elevation cross-section view of the device of the present invention, according to said third embodiment, comprising venting means according to a first option.
Figure 6:
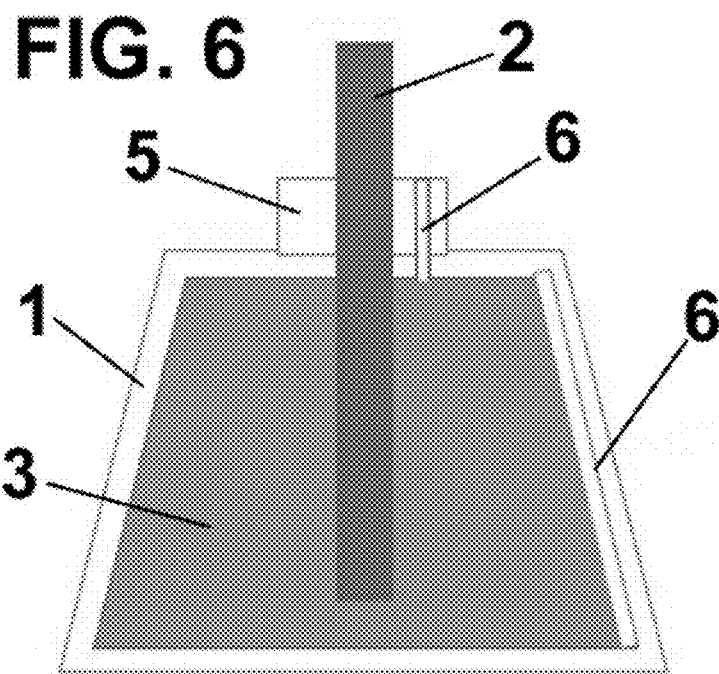
FIG. 6 is a diagrammatical elevation cross-section view of the device of the present invention, according to said third embodiment, comprising venting means according to a second option.

The device according to the present invention can also comprise venting means for venting the container 1, as shown in FIGS. 5 and 6.

In FIG. 5 the venting means comprises two vents 6, which are placed on a top and bottom portion of the container 1, for balancing the pressure inside the container 1.

In FIG. 6 the venting means comprises also two vents 6, one placed on the top portion of the container 1 and the other placed on the side portion of the container 1. This vent 6 placed on the side portion of the container 1 is preferably a channel made on the container itself or on the porous element 3.

The vents 6 can be closed in any suitable way, e.g. with the stopper 5 or with an impermeable label (not shown).

Figure 7:
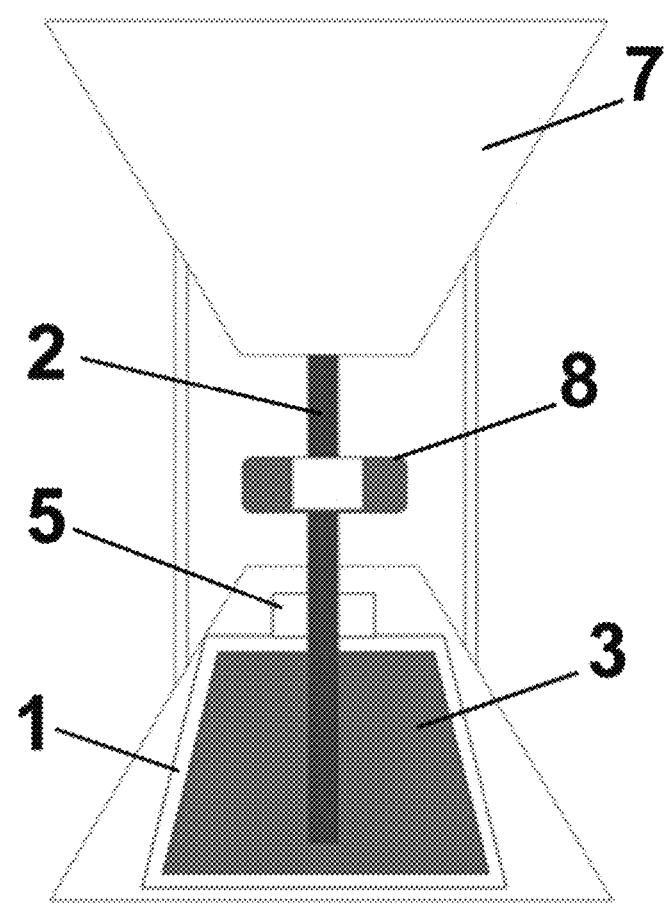
FIG. 7 is a diagrammatical elevation cross-section view of the device of the present invention, according to said fourth embodiment, comprising an additional body and a heater.

FIG. 7 shows a fourth embodiment of the device according to the present invention. According to this embodiment, the device comprises an additional body 7 having a shape that matches with the shape of the container 1 (or with the shape of a housing that houses the container 1) and placed symmetrically with respect to the wick 2.

According to this embodiment, the device also comprises preferably a heater 8 placed close or next to the wick 2, in particular, placed equidistantly from the container 1 and the additional body 7.

Even though reference has been made to a specific embodiment of the invention, it is obvious for a person skilled in the art that the device described herein is susceptible to numerous variations and modifications, and that all of the details mentioned can be substituted for other technically equivalent ones without departing from the scope of protection defined by the attached claims.

The invention claimed is:
1. Device for evaporating volatile substances, comprising:
a container (1) housing a liquid with the volatile substances, and
a wick (2) in contact with said liquid and extending outside said container (1), characterized in that the device also comprises a porous element (3) placed inside the container (1) that is impregnated with said liquid with the volatile substances,
wherein the device also comprises venting means (6) for venting the container (1), and wherein the venting means comprises a plurality of vents (6) placed on the top and bottom portions of the container (1) and/or on the side portion of the container (1).

2. Device for evaporating volatile substances according to claim 1, wherein all the liquid is impregnated in the porous element (3).

3. Device for evaporating volatile substances according to claim 1, wherein the porous element (3) is a sponge.

4. Device for evaporating volatile substances according to claim 1, wherein the porous element (3) is made from a polymeric substrate.

5. Device for evaporating volatile substances according to claim 1, wherein the container (1) comprises a cover (4).

6. Device for evaporating volatile substances according to claim 1, wherein a cover (4) or container (1) comprises a hole through which said wick (2) is passed.

7. Device for evaporating volatile substances according to claim 6, wherein the cover (4) or container (1) comprises a stopper (5) placed around the hole in contact with the wick (2).

8. Device for evaporating volatile substances according to claim 1, wherein the porous element (3) is compressed inside the container (1).

9. Device for evaporating volatile substances according to claim 1, wherein the wick (2) extends substantially along the whole container (1).

10. Device for evaporating volatile substances according to claim 1, wherein the venting means further comprises a vent (6) of the plurality of vents (6) placed on a stopper (5).

11. Device for evaporating volatile substances according to claim 1, wherein the device also comprises an additional body (7) placed symmetrically with respect to the wick (2), the additional body having an external geometry similar to the container.

12. Device for evaporating volatile substances according to claim 1, wherein the device also comprises a heater (8).

13. Device for evaporating volatile substances according to claim 12, wherein the heater (8) is placed close or next to the wick (2).

14. Device for evaporating volatile substances according to claim 13, wherein the heater (8) is placed substantially equidistantly from the container (1) and an additional body (7).

15. Device for evaporating volatile substances according to claim 9, wherein the venting means further comprises a vent (6) of the plurality of vents (6) placed on a stopper (5).

16. Device for evaporating volatile substances according to claim 9, wherein the device also comprises an additional body (7) placed symmetrically with respect to the wick (2), the additional body having an external geometry similar to the container.

\* \* \* \* \*